(12) United States Patent
Bydlinski et al.

(10) Patent No.: US 7,442,813 B2
(45) Date of Patent: Oct. 28, 2008

(54) PROCESS FOR PRODUCING DIOXOLANE NUCLEOSIDE ANALOGUES

(75) Inventors: Gregory Bydlinski, Montreal (CA); Qing Yu, Laval (CA); Alex Cimpoia, Verdun (CA)

(73) Assignee: Shire Biochem Inc., Quebec (CA)

( * ) Notice: Subject to any disclaimer, the term of this patent is extended or adjusted under 35 U.S.C. 154(b) by 0 days.

(21) Appl. No.: 11/713,724

(22) Filed: Mar. 5, 2007

(65) Prior Publication Data
US 2007/0197784 A1 Aug. 23, 2007

Related U.S. Application Data

(62) Division of application No. 10/502,440, filed as application No. PCT/CA03/00085 on Jan. 23, 2003, now abandoned.

(60) Provisional application No. 60/350,968, filed on Jan. 25, 2002.

(51) Int. Cl.
*C07D 317/20* (2006.01)
(52) U.S. Cl. ...................................... 549/449
(58) Field of Classification Search .................. 549/449
See application file for complete search history.

(56) References Cited

U.S. PATENT DOCUMENTS

| 5,693,787 | A | 12/1997 | Arshad et al. |
| 5,922,867 | A | 7/1999 | Krzystof et al. |
| 6,350,753 | B1 | 2/2002 | Belleau et al. |
| 2006/0036092 | A1 | 2/2006 | Sznaidman et al. |
| 2006/0134763 | A1 | 6/2006 | Cimpoia et al. |

FOREIGN PATENT DOCUMENTS

| EP | 0515156 | 11/1992 |
| WO | WO 9214729 | 9/1992 |

OTHER PUBLICATIONS

Evans, Colleen A. et al: "Divergent asymmetric syntheses of dioxolane nucleoside analogs" Tetrahedron: Asymmetry (1993), 4(11), 2319-22, 1993 XP001145856.

Jin, Haolun et al: "Unexpected effects of Lewis acids in the synthesis of optically pure 2'-deoxy-3'-oxacytidine nucleoside analogs" Tetrahedron: Asymmetry (1993), 4(2), 211-14, 1993, XP001145857.

Sorensen et al, J Am Chem. Soc; 2002; 124(10) pp. 2164-2176, and Supplemental pp. S1-S31.

*Primary Examiner*—Taofiq A Solola
(74) *Attorney, Agent, or Firm*—Millen, White, Zelano, Branigan, P.C.

(57) ABSTRACT

The present invention relates to a process conducted in a single reaction vessel for producing a dioxolane nucleoside analogue of formula I or a pharmaceutically acceptable salt thereof; the process comprising the steps of adding a Lewis acid, a silylating agent and a non-silylated purine or pyrimidine base or an analogue thereof to a dioxolane of formula II. The invention also provides a process for producing a dioxolane compound of formula III; by reacting a dioxolane compound of formula IV in a suitable solvent in the presence of DIB and $I_2$, using a suitable source of energy.

26 Claims, 2 Drawing Sheets

PROCESS FOR PRODUCING DIOXOLANE NUCLEOSIDE ANALOGUES

This application claims the benefit of U.S. provisional application Ser. No. 60/350,968, filed Jan. 25, 2002 now abandoned.

This application is a divisional of U.S. application Ser. No. 10/502,440, which is a 35 USC 371 national phase Application of PCT/CA03/00085, filed Jan. 23, 2003.

FIELD OF THE INVENTION

The present invention relates to a process for producing dioxolane nucleoside analogues and their precursors.

BACKGROUND OF THE INVENTION

Nucleoside analogues are an important class of therapeutic agents. More particularly, dioxolane nucleoside analogues in which a substituted 1,3-dioxolane is replacing the carbohydrate found in natural nucleoside have shown to have biological activity.

Dioxolane analogues were first reported by Belleau et al. in EP 0337713 published Oct. 19, 1989, in U.S. Pat. No. 5,041,449 issued Aug. 20, 1991 and U.S. Pat. No. 5,270,315 issued Dec. 14, 1993.

9-($\beta$-D-2-hydroxymethyl-1,3-dioxolane-4-yl)-2,6-diaminopurine ($\beta$-D-DAPD) and 9-($\beta$-D-hydroxymethyl 1,3-dioxolane-4-yl)-9-guanine ($\beta$-D-DXG) have been reported by Gu et al. (*Antimicrob. Agents Chemother.* (1999), 43(10), pp 2376-2382 and *Nucleosides Nucleotides* (1999), 18(4&5), pp 891-892) to have useful efficacy against HIV-1 in various cell system.

Additionally, it was also reported (Weitman et al *Clinical Cancer Research* (2000), 6(4), pp 1574-1578 and Giles et al *Journal of Clinical Oncology* (2001), 19(3), pp 762-771 and also Gourdeau et al *Cancer Chemother. Pharmacol.* (2001), 47(3), pp 236-240) that 1-($\beta$-L-2-hydroxymethyl-1,3-dioxolane-4-yl)-cytosine ($\beta$-L-OddC, troxacitabine) have shown efficacy for the treatment of various forms of cancers (e.g. solid tumours, adult leukemia and lymphomas).

DAPD and troxacitabine are currently in clinical development. The production of drug compound has to deal with issues such as cost and efficacy, as well as, environmental concerns and management of waste. Although several methods exist for the production of dioxolane nucleoside analogues, there is always a need for further development of new chemical processes for producing such compounds.

SUMMARY OF THE INVENTION

In one aspect, the present invention relates to a process conducted in a single reaction vessel for producing a dioxolane nucleoside analogue of formula I or a pharmaceutically acceptable salt thereof;

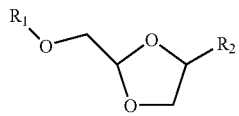

the process comprising the steps of adding:
a) a Lewis acid;
b) a silylating agent; and
c) a non-silylated purine or pyrimidine base or an analogue thereof;
to a dioxolane of formula II in a suitable solvent;

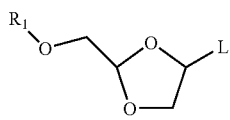

wherein;
$R_1$ is a hydroxyl protecting group;
$R_2$ is a purine or pyrimidine base or an analogue thereof;
L is a leaving group; and wherein said process is conducted at a suitable temperature.

In another aspect, there is provided a process for producing a dioxolane compound of formula III:

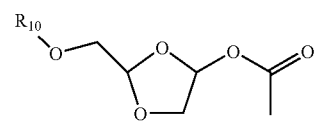

the process comprising the step of reacting a dioxolane compound of formula IV in a suitable solvent;

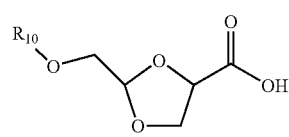

in the presence of DIB and $I_2$, wherein said process is conducted using a suitable source of energy; wherein $R_{10}$ is an hydroxyl protecting group.

DETAILED DESCRIPTION OF THE INVENTION

The present invention relates to a process conducted in a single reaction vessel for producing a dioxolane nucleoside analogue of formula I or a pharmaceutically acceptable salt thereof;

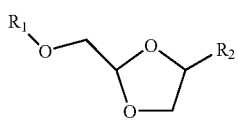

the process comprising the steps of adding:
a) a Lewis acid;
b) a silylating agent; and
c) a non-silylated purine or pyrimidine base or an analogue thereof;
to a dioxolane of formula II in a suitable solvent;

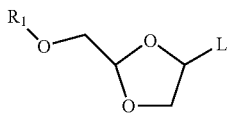

wherein;

$R_1$ is a hydroxyl protecting group;

$R_2$ is a purine or pyrimidine base or an analogue thereof;

L is a leaving group; and wherein said process is conducted at a suitable temperature.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

As used in this application, the term "alkyl" represents an unsubstituted or substituted (e.g. by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "alkoxy" represents an alkyl which is covalently bonded to the adjacent atom through an oxygen atom.

The term "aryl" represents an unsaturated carbocyclic moiety, optionally mono- or di-substituted with OH, SH, amino, halogen or $C_{1-6}$ alkyl.

The term "arylalkyl" represents an aryl group attached to the adjacent atom by a $C_{1-6}$ alkyl (e.g., benzyl).

The term "aryloxy" represents an aryl which is covalently bonded to the adjacent atom through an oxygen atom.

The term "Acyl" is defined as a radical derived from a carboxylic acid, obtained by replacement of the —OH group. Like the acid to which it is related, an acyl radical may be straight chain, branched chain or cyclic aliphatic or aromatic, substituted (e.g. by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) or unsubstituted, Useful examples of acyl includes acetyl, propionyl, pivaloyl, hexanoyl, trifluoroacetyl, cyclohexanoyl and benzoyl.

"Acyloxy" is defined as an acyl group attached to the adjacent group by an oxygen atom (e.g. acetoxy, benzoyloxy).

As used in this application, the term "cycloalkyl" represents an "alkyl" as defined above which forms a ring (e.g. Cyclopropyl, cyclopentyl or cyclohexyl)

The term "cycloalkylamino" represents a cycloalkyl which is covalently bonded to the adjacent atom through a nitrogen atom.

The term "hydroxyl protecting group" is well known in the field of organic chemistry. Such protecting groups may be found in T. Greene, *Protective Groups In Organic Synthesis*, (John Wiley & Sons, 1981). Example of hydroxy protecting groups include but are not limited to benzyl, acetyl, benzoyl, pivaloyl and isopropyloxycarbonyl.

A "dioxolane ring" is any substituted or unsubstituted five member monocyclic ring that has an oxygen in the 1 and 3 positions of the ring as illustrated below:

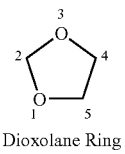

Dioxolane Ring

Halogens are chosen from F, Cl, I, and Br.

As used in this application, the term "purine or pyrimidine or an analogue" is meant to be a purine or pyrimidine base found in a nucleotide or an analogue thereof which mimics such bases in that their structures (the kinds of atoms and their arrangement) are similar to the normal bases but may possess additional or lack certain of the functional properties of the normal bases. Such analogues include those derived by replacement of a CH moiety by a nitrogen atom (for example, 5-azapyrimidines such as 5-azacytosine) or vice versa (for example 7-deazapurines, such as 7-deazaadenosine or 7-deazaguanosine) or both (e.g. 7-deaza, 8-azapurines). Analogues of such bases also include those compounds wherein ring substituents are either incorporated, removed or modified by conventional substituents known in the art e.g. halogen, hydroxyl, amino, C1-6 alkyl. Such purine or pyrimidine bases, analogues and derivatives will be well known to those skilled in the art.

The term "TMSI" means trimethylsilyl iodide.

The term "HMDS" means hexamethyldisilazane.

The term "DIB" means diacetoxy iodobenzene.

The term "leaving group" means a functional group that is cleaved from the parent molecule under the reaction conditions.

The term "single reaction vessel" means the chemical reactions involved in the process are conducted in one vessel typically used for chemical synthesis.

The term "Lewis acid" is well known in the field of nucleoside and nucleotide chemistry. Such Lewis acid may be found in *Chemistry of NUCLEOSIDES AND NUCLEOTIDES* Vol 1 and Vol 2., (Edited by LEROY B. TOWNSEND, 1988). Examples of a Lewis acid includes but are not limited to trimethylsilyl triflate and TMSI.

The term "suitable solvent" means an inert organic solvent that will allow the process to occur under the reaction conditions (e.g. dichloromethane).

The term "suitable temperature" means a temperature that will allow the process to occur under the reaction conditions, and provide the desired product without adversely affecting the reaction.

It will be appreciated by a person of skill in the art that the term "suitable period of time" means the time necessary for obtaining a sufficient chemical transformation of the starting material, obtaining the desired purity or the desired yield of the reaction product or a combination of those. The reaction can typically be monitored, if desired, by thin layer chromatography or high performance liquid chromatography (HPLC).

It will also be appreciated that TMSI can be obtained from a commercial source or be prepared readily from a number of precursor reagents (e.g. trimethylsilyl chloride and sodium iodide).

The term "suitable source of energy" means a source of energy useful to carry out the desired chemical process without adversely affecting the reaction. Examples of energy include but are not limited to light (e.g. daylight or tungsten lamp light) or heat.

It will be appreciated by those skilled in the art that compound I, compound Ia, compound II, compound III and compound IV contain at least two chiral centers (at C-2 and C-4 of the dioxolane ring). The compounds can thus exist in the form of different optical isomers (R and S) and geometric isomers (cis and trans). All such optical isomers, geometric isomers and mixtures thereof, including racemic mixtures are included within the scope of the invention.

In one embodiment, the process of the present invention comprises those wherein the following embodiments are present, either independently or in combination.

In one embodiment of the invention, the Lewis acid is chosen from $SnCl_4$, $AlCl_3$, trimethylsilyl triflate, trimethylsilyl nonaflate, trimethylsilyl perchlorate, TMSI, TMSCl, TMSBr or $TiCl_4$.

In one embodiment, the Lewis acids have the formula V:

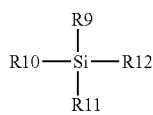

wherein $R_9$, $R_{10}$ and $R_{11}$ are independently selected from the group consisting of hydrogen; $C_{1-20}$ alkyl (e.g. methyl, ethyl, ethyl, t-butyl), optionally substituted by halogens (F, Cl, Br, I), $C_{6-20}$ alkoxy (e.g., methoxy) or $C_{6-20}$ aryloxy (e.g., phenoxy); $C_{7-20}$ aralkyl (e.g., benzyl), optionally substituted by halogen, $C_{1-20}$ alkyl or $C_{1-20}$ alkoxy (e.g., p-methoxybenzyl); $C_{6-20}$ aryl (e.g., phenyl), optionally substituted by halogens, $C_{1-20}$ alkyl or $C_{1-20}$ alkoxy; trialkylsilyl; fluoro; bromo; chloro and iodo; and $R_{12}$ is selected from the group consisting of halogen (F, Cl, Br, I) preferably I (iodo);

In another embodiment, the Lewis acid is TMSI.

In one embodiment, L is chosen from acetoxy, benzoyloxy or iodide.

In one embodiment, L is acyloxy.

In one embodiment, L is acetoxy.

In one embodiment, L is benzoyloxy.

In one embodiment L is a halogen.

In one embodiment, L is iodide.

In one embodiment of the invention, $R_1$ is chosen from $C_{1-6}$ alkyl, $C_{6-12}$ aryl, $C_{6-12}$ arylalkyl, CO—$C_{1-6}$ alkyl, CO—$C_{1-6}$ alkoxy, CO—$C_{6-12}$ aryloxy, or CO—$C_{6-12}$ arylalkyl.

In one embodiment of the invention, $R_1$ is chosen from acetyl, pivaloyl, benzoyl or benzyl.

In one embodiment of the invention, $R_1$ is benzoyl.

In one embodiment, the suitable temperature is about $-78°$ C. or warmer.

In another embodiment, the suitable temperature is about $-15°$ C. or warmer.

In still another embodiment, the suitable temperature is about room temperature.

In one embodiment, the Lewis acid is TMSI, and said Lewis acid is used in a molar ratio of about 1.0 equivalent to about 2.0 equivalents with respect to the dioxolane of formula II.

In a further embodiment, TMSI is used in a molar ratio of about 1.0 equivalent to about 1.5 equivalents with respect to the dioxolane of formula II.

In still a further embodiment, TMSI is used in a molar ratio of about 1.0 equivalent to about 1.2 equivalents with respect to the dioxolane of formula II.

In one embodiment of the invention, the process for producing a dioxolane nucleoside of formula I comprises the steps of:
 a) first adding TMSI to a solution of the dioxolane of formula II and allowing the resulting mixture to react for a suitable period of time; and
 b) adding the silylating agent and the purine or pyrimidine base $R_2$ to the mixture resulting from step a).

In one embodiment, the silylating agent is chosen from HMDS, bis(trimethylsilyl)acetamide, TMSI, trimethylsilyl chloride, tButyl-dimethylsilyl trifluoromethanesulfonate or trimethylsilyl trifluoromethanesulfonate.

In a further embodiment, the silylating agent is HMDS.

In one embodiment, the silylating agent is used in a molar ratio of about 1.0 equivalent to about 5.0 equivalents with respect to the purine and pyrimidine base $R_2$.

In one embodiment, the silylating agent is used in a molar ratio of about 1.0 equivalent to about 2.5 equivalents with respect to the purine and pyrimidine base $R_2$.

In one embodiment, the silylating agent is used in a molar ratio of about 1.0 equivalent to about 1.5 equivalents with respect to the purine and pyrimidine base $R_2$.

In one embodiment, $R_2$ is chosen from:

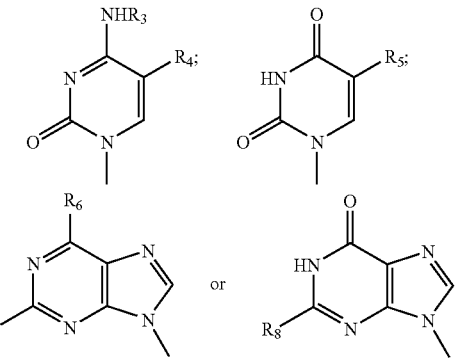

wherein;

$R_3$ is chosen from H, $C_{1-6}$ alkyl, $C_{1-6}$ acyl and CO—$R_9$;

wherein $R_9$ is H or $C_{1-6}$ alkyl;

$R_4$ and $R_5$ are each independently chosen from H, $C_{1-6}$ alkyl, bromide, chloride, fluoride, iodide or $CF_3$; and $R_6$, $R_7$ and $R_8$ are each independently chosen from H, bromide, chloride, fluoride, iodide, amino, hydroxyl or $C_{3-6}$ cycloalkylamino.

In another embodiment, $R_2$ is chosen from:

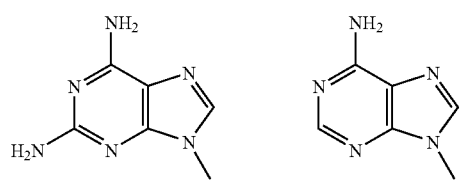

-continued

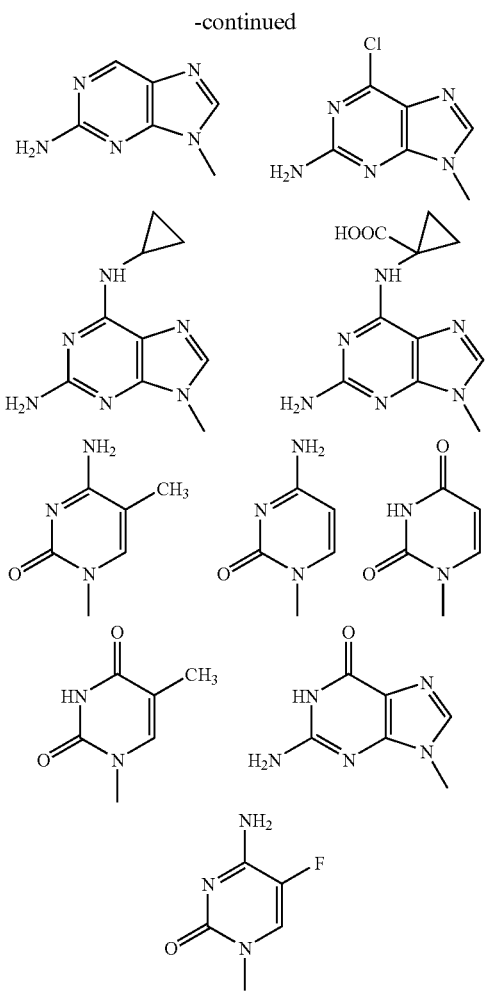

In one embodiment, $R_2$ is:

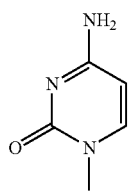

In a further embodiment, $R_2$ is:

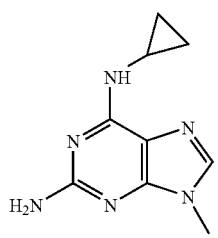

In one embodiment of the invention, the process for producing a dioxolane nucleoside of formula I further comprises the step of removing the protecting group $R_1$ to produce a compound of formula Ia or a pharmaceutically acceptable salt thereof;

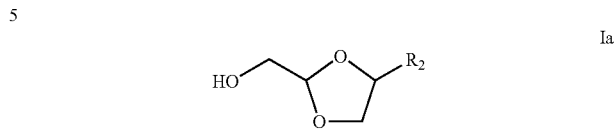

According to another aspect of the invention, there is provided a process for producing a dioxolane compound of formula III:

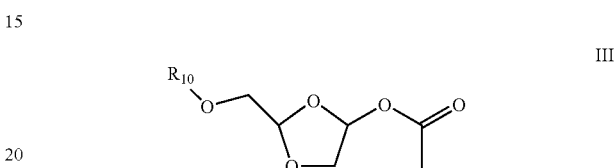

the process comprising the step of reacting a dioxolane compound of formula IV in a suitable solvent;

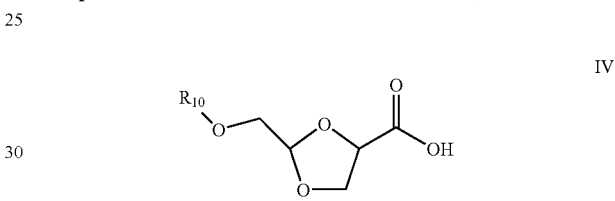

in the presence of DIB and $I_2$, wherein said process is conducted using a suitable source of energy; and wherein $R_{10}$ is an hydroxyl protecting group.

In one embodiment of the invention, the dioxolane compound of formula IV is added to a mixture of DIB and $I_2$ over a suitable period of time.

In a further embodiment of the invention, the dioxolane compound of formula IV is added to a mixture of DIB, $I_2$ and acetic acid over a suitable period of time.

In one embodiment, $R_{10}$ is chosen from $C_{1-6}$ alkyl, $C_{6-12}$ aryl, $C_{6-12}$ arylalkyl, CO—$C_{1-6}$ alkyl, CO—$C_{1-6}$ alkoxy, CO—$C_{6-12}$ aryloxy, or CO—$C_{6-12}$ arylalkyl.

In one embodiment, $R_{10}$ is chosen from acetyl, pivaloyl, benzoyl or benzyl.

In one embodiment, $R_{10}$ is benzoyl.

In one embodiment, the suitable solvent for the process for producing a dioxolane compound of formula III is toluene or dichloromethane.

In a further embodiment, the suitable solvent is dichloromethane.

In a further embodiment of the invention, DIB is used in a molar ratio of about 1.0 equivalent to about 2.5 equivalents with respect to the dioxolane compound of formula III.

In still a further embodiment, DIB is used in a molar ratio of about 1.1 equivalent to about 1.5 equivalents with respect to the dioxolane compound of formula III.

In one embodiment, $I_2$ is used in a molar ratio of about 0.1 equivalent to about 1.0 equivalent with respect to the dioxolane compound of formula III.

In one embodiment, $I_2$ is used in a molar ratio of about 0.3 equivalent to about 0.5 equivalent with respect to the dioxolane compound of formula III.

In one embodiment, the suitable source of energy is light.

In a further embodiment, the suitable source of energy is tungsten lamp light.

In still a further embodiment, the suitable source of energy is daylight.

In one embodiment, the suitable source of energy is heat.

There is also provided pharmaceutically acceptable salts of the compounds of formula I and formula Ia of the present invention. The term pharmaceutically acceptable salts of the compounds of formula I and formula Ia is meant to include those compounds derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4+$ (where R is $C_{1-4}$ alkyl) salts.

The following examples are provided to illustrate various embodiments of the present invention and shall not be considered as limiting in scope. Useful intermediates in those synthesis are prepared according to known procedures described in:

1) PCT publication number WO 00/39143 by NGUYEN-B A, Nghe et al. 6 Jul. 2000
2) PCT publication number WO 00/47759 by CIMPOIA, Alex et al. 17 Aug. 2000
3) U.S. Pat. No. 6,022,876 by CHUNG, K. Chu et al Feb. 8, 2000
4) U.S. Pat. No. 5,817,667 by CHUNG, K. Chu et al Oct. 6, 1998

EXAMPLES

Example 1

Figure 1:
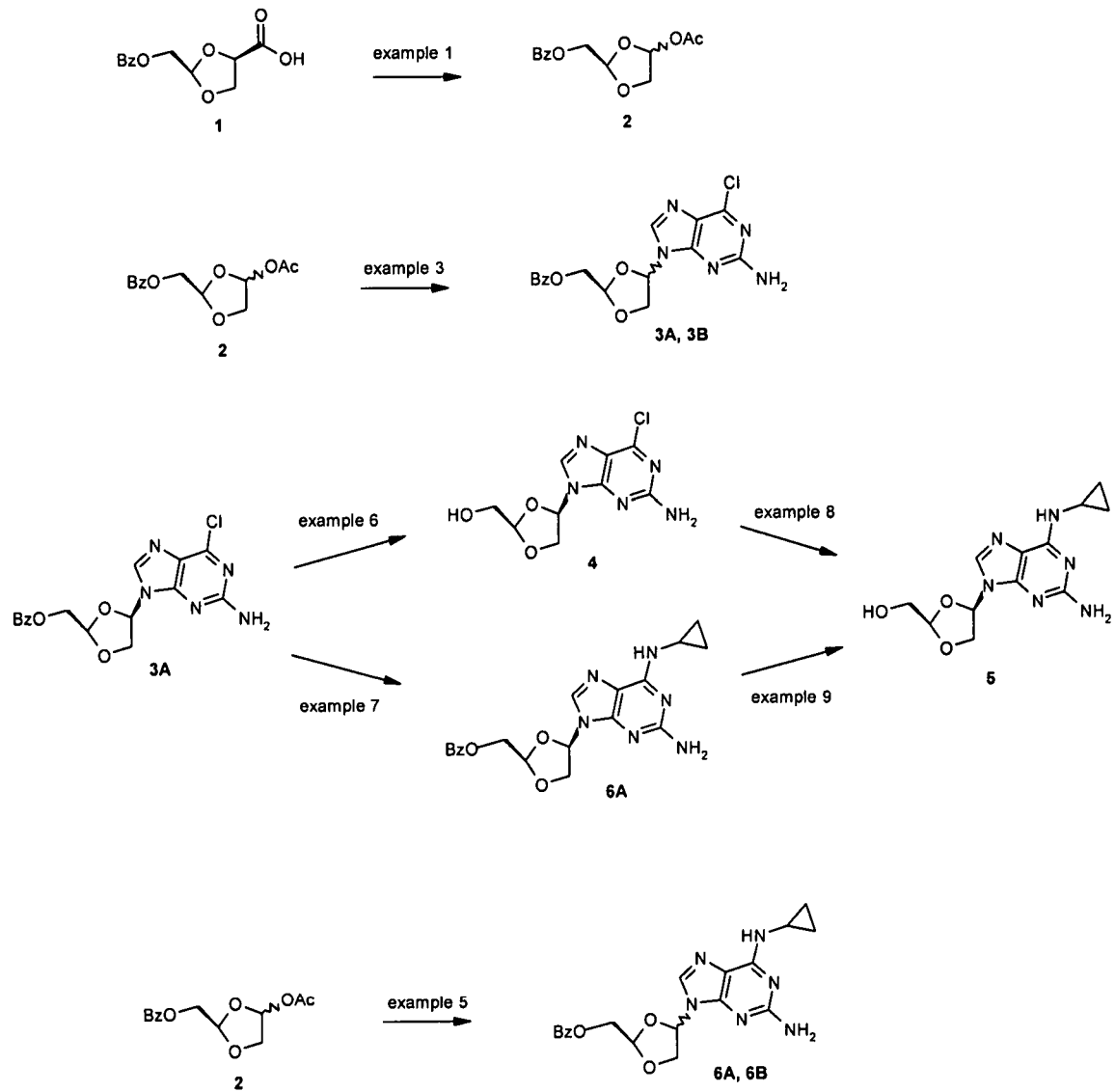
FIG. 1 illustrates the reaction schemes for Examples 1, 3, and 5-9.
Figure 2:
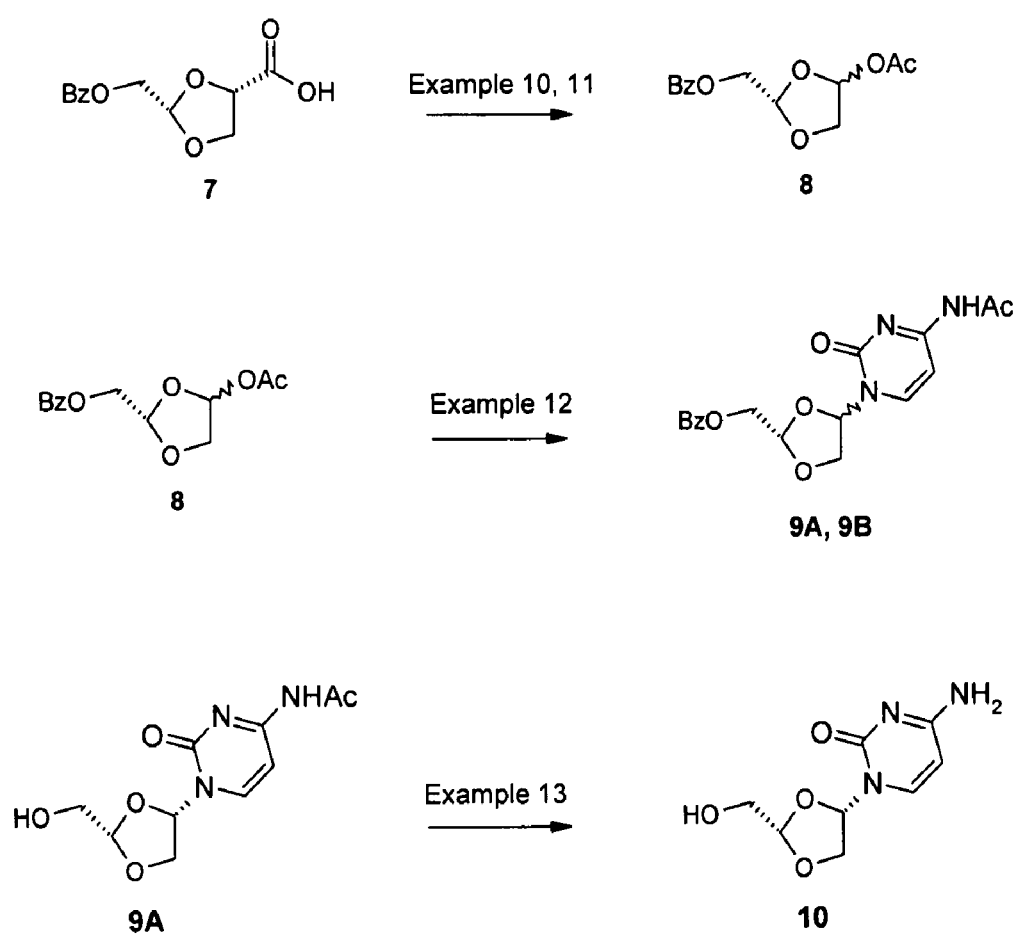
FIG. 2 illustrates the reaction schemes for Examples 10-13.

Preparation of Benzoic acid 4(R,S)-acetoxy-[1,3]dioxolan-2(R)-ylmethyl ester (compound 2)

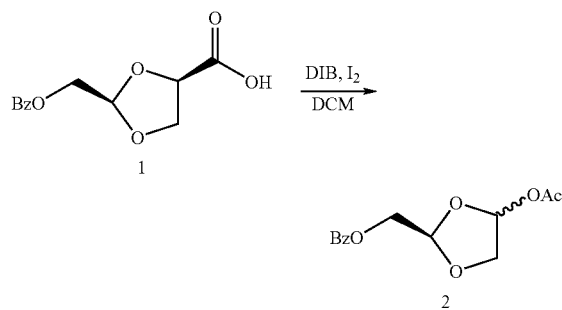

Intermediate 1 can be prepared according to known procedures described in PCT publication number WO 00/39143 by NGUYEN-B A, Nghe et al. 6 Jul. 2000 and PCT publication number WO 00/47759 by CIMPOIA, Alex et al. 17 Aug. 2000.

To a solution of DIB (6.36 g, 19.8 mmol) and iodine (1.368 g, 5.4 mmol) in dichloromethane (24 mL) at room temperature was added a solution of 2(R)-Benzoyloxymethyl-[1,3]dioxolane-4(R)-carboxylic acid (5.04 g, 18 mmol) in dichloromethane (27 mL) over 2.5 hours. The solution was then stirred for an additional 4 hours at room temp. The reaction was quenched with a solution of sodium thiosulfate pentahydrate (4.92 g, 18 mmol) in water (50 mL) and stirred for 15 minutes. The layers where allowed to separate and the organic phase was collected. The aqueous phase was extracted with dichloromethane (25 mL) and the organic phases were combined and dried over sodium sulfate. The sodium sulfate was removed and the solvent was evaporated to dryness. The crude product was placed under high-vacuum overnight. The crude oil was column purified with (EtOAc/Hex:1/3) to give 4.24 g. (88.5% yield) (HPLC 99%)

(Trans) Benzoic acid 4(S)-acetoxy-[1,3]dioxolan-2(R)-ylmethyl ester, δ ($CDCl_3$); 8.08 (d, 2H), 7.58 (m, 1H), 7.47 (m, 2H), 6.40 (d, 1H), 5.48 (t, 1H), 4.49 (m, 2H), 4.20 (d, 1H), 4.06 (d of d, 1H), 2.02 (s, 3H): (Cis) Benzoic acid 4(R)-acetoxy-[1,3]dioxolan-2(R)-ylmethyl ester, δ ($CDCl_3$); 8.05 (d, 2H), 7.55 (m, 1H), 7.45 (m, 2H), 6.47 (d, 1H), 5.57 (t, 1H), 4.47 (d, 2H), 4.24 (d of d, 1H), 4.00 (d of d, 1H), 2.11 (s, 3H).

Example 2

Preparation of benzoic acid 4(R,S)-(2-amino-6-chloro-purin-9-yl)-[1,3]dioxolan-2(R)-ylmethyl ester (Compound 3A and 3B)

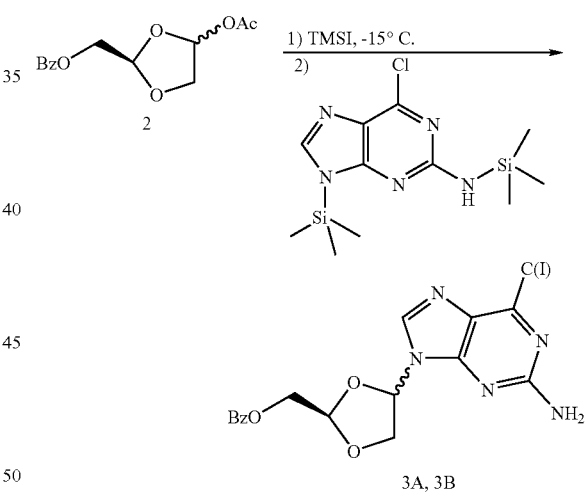

TMSI (28.2 mL, 198.12 mol eq.) was added dropwise to a dichloromethane (750 mL) solution of benzoic acid 4-acetoxy-[1,3]dioxolan-2(R)-ylmethyl ester (52.75 g, 198.12 mmol, 1 eq) at −15° C. After 2.5 h at −15° C., bissilylated 2-amino-6-chloropurine (62 g, 198 mmol, 1 eq) was added to the reaction mixture as a solid and the stirring was continued at the same temperature for another 2.5 h. The reaction mixture was then allowed to warm up slowly to RT with continued stirring for 40 h. The reaction mixture was quenched into a saturated aqueous $NaHCO_3$ solution (1 L). The mixture was treated with $Na_2S_2O_3$ (1 g) and stirred for 20 min. The mixture was filtered through a small pad of celite. The organic phase was separated and the aqueous phase was back-extracted with dichloromethane (1×200 mL). The combined organic phase was concentrated to give 87 g of the crude product. Column purification (DCM/MeOH:96/4) of the crude yielded 67.7 g (81% assuming that it is a 1:1 chloro/Iodo mixture at C-6) of the coupled product with cis/trans ratio 2.3:1.

Cis 6-chloropurine dioxolane δ (CDCl$_3$); 8.05 (s, 1H), 8.00 (d, 2H), 7.58 (m, 1H), 7.44 (m, 2H), 6.38 (d, 1H), 5.43 (t, 1H), 5.18 (bs, 2H), 4.68 (m, 3H), 4.31 (d of d, 1H): Cis 6-iodopurine dioxolane δ (DMSO); 8.13 (s, 1H), 7.82 (d, 2H), 7.68 (t, 1H), 7.52 (m, 2H), 6.92 (bs, 2H), 6.28 (d, 1H), 5.38 (t, 1H), 4.75 (d, 1H), 4.46 (m, 2H), 4.28 (m, 1H): Trans 6-chloropurine dioxolane δ (CDCl$_3$); 8.08 (d, 2H), 7.95 (s, 1H), 7.60 (m, 1H), 7.47 (m, 2H), 6.43 (t, 1H), 5.85 (t, 1H), 5.21 (bs, 2H), 4.50 (m, 4H): Trans 6-iodopurine dioxolane δ (DMSO); 8.22 (s, 1H), 8.00 (d, 2H), 7.68 (t, 1H), 7.52 (m, 2H), 6.92 (bs, 2H), 6.37 (m, 1H), 5.84 (m, 1H), 4.50 (m, 4H).

Example 3

Preparation of Benzoic acid 4(R)-(2-amino-6-chloropurin-9-yl)-[1,3]dioxolan-2(R)-ylmethyl ester (Compound 3A)

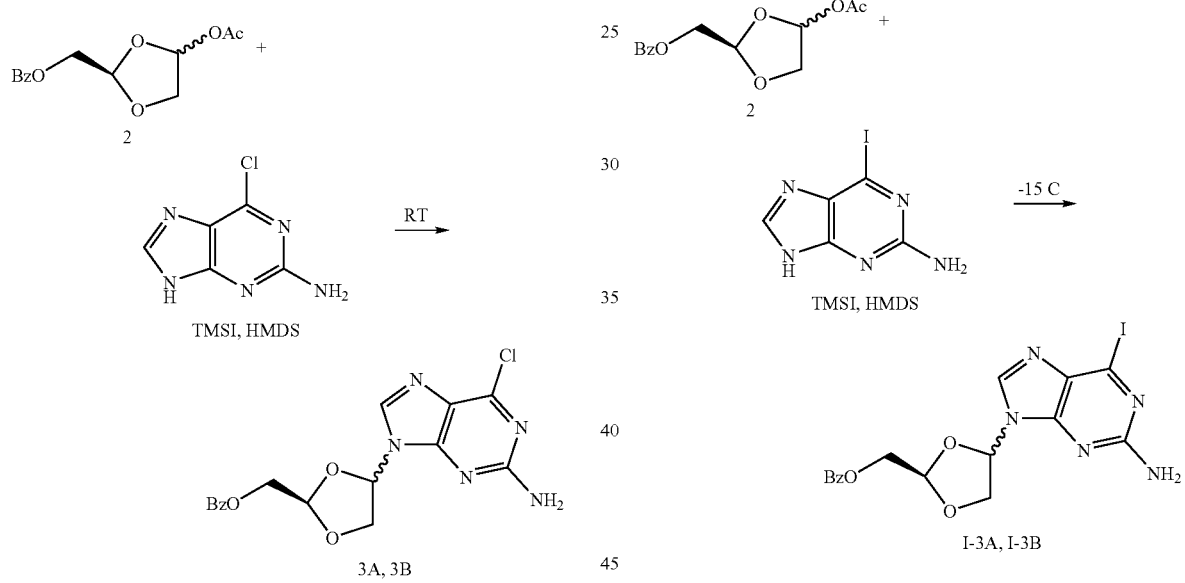

Hexamethyldisilazane (HMDS, 190 g, 1.18 moles) is charged to a solution of 2-(R)-Benzoyloxymethyl-4-(R,S)-acetoxy-1,3-dioxolane (311 g, 1.17 moles) in dichloromethane (6.75 kg), followed by 2-amino-6-chloropurine (199 g, 1.17 moles) and trimethylsilyl iodide (TMSI, 280 g, 1.40 moles). The reaction mixture is agitated at 19-25° C. for 19-24 hr. The reaction is checked by in-process TLC (2:1/hexane:ethyl acetate) for complete reaction. The reaction mixture is heated at reflux for 1 hr. Aqueous 2% sodium thiosulfate solution (3.6 kg) is then added to the reaction mixture at 10-15° C. and agitated for 30-60 minutes. The reaction mixture is checked by in-process TLC (7:3 v/v ethyl acetate/hexane) for complete deprotection. Aqueous 10% sodium hydroxide solution (737 g) is added to the mixture to adjust the pH to 8-10. The organic layer is separated. The aqueous layer is extracted with dichloromethane (750 g). The organic layers are combined, dried over magnesium sulfate (95 g) and filtered. The filter cake is washed with dichloromethane (750 g). The combined organic filtrate is distilled until distillation stops at 45-50° C. An in-process TDS is performed and the amount of dissolved solid (Q) calculated from the TDS value. Ethyl acetate (534 g) is added to the pot residue and distilled under partial vacuum at a maximum pot temperature of 50° C. The ethyl acetate distillation is repeated until a total of 1.3×Q of ethyl acetate distillate is obtained. Toluene (700 g) is added to the pot residue. The mixture is agitated at 19-25° C. for 16-24 hours and at 0-5° C. for 2-3 hours. The precipitate is filtered and the filter cake washed with 10% ethyl acetate/hexane (300 g). The solid product is dried under vacuum at 40-45° C. to yield 284 g (64.0% total yield) of a 2/1 cis (3A) to trans (3B) mixture (yield 3A cis: 42%). The isomers were separated by column chromatography on silica gel, using a gradient of methanol from 1% to 5% in dichloromethane.

Example 4

Preparation of Benzoic acid 4(R,S)-(2-amino-6-iodopurin-9-yl)-[1,3]dioxolan-2(R)-ylmethyl ester (Compound I-3A)

2-(R)-Benzoyloxymethyl-4-(R,S)-acetoxy-1,3-dioxolane (12.98 g, 40 mmol) in methylene chloride (200 mL) was cooled to −15° C. under argon atmosphere and TMSI (6.85 mL, 48 mmol, 1.2 eq) was added with stirring. The light yellow solution was stirred at −15° C. until all the starting material had disappeared (2 hours) by TLC (DCM/MeOH:9/1). HMDS (12.6 mL, 60 mmol, 1.5 eq) was added followed by the addition of 2-amino-6-iodopurine (11.5 g, 44 mmol, 1.1 eq). The light yellow suspension obtained was stirred at −15° C. (2 hours) and at 23° C. (20 hours) at which time TLC indicated that the reaction was completed. The mixture was diluted with methylene chloride (150 mL) and poured into water (200 mL). The mixture was vigorously stirred (3 hours) and the phases were separated. The organic phase was washed with aqueous 10% K$_2$SO$_4$ (20 mL) and water (50 mL) The organic phase was evaporated to a brown residue. The residue was dissolved in methanol (200 ml). After stirring at 23° C. for 2 hours TLC showed that complete desilylation had occurred. The methanol was evaporated under reduced pressure to give a residue which contains Benzoic acid 4(R,S)-(2-amino-6-iodo-purin-9-yl)-[1,3]dioxolan-2(R)-ylmethyl ester (20.1 g, cis/trans:2.8/1). Cis iodopurine dioxolane δ (DMSO); 8.13 (s, 1H), 7.82 (d, 2H), 7.68 (t, 1H), 7.52 (m, 2H), 6.92 (bs, 2H), 6.28 (d, 1H), 5.38 (t, 1H), 4.75 (d, 1H), 4.46 (m, 2H), 4.28 (m, 1H): Trans iodopurine dioxolane δ (DMSO); 8.22 (s, 1H), 8.00 (d, 2H), 7.68 (t, 1H), 7.52 (m, 2H), 6.92 (bs, 2H), 6.37 (m, 1H), 5.84 (m, 1H), 4.50 (m, 4H)

0.65 (m, 2H). Trans Benzoic acid 4(S)-(2-amino-6-cyclopropylamino-purin-9-yl)-[1,3]dioxolan-2(R)-ylmethyl ester, ☐ (CDCl₃); 8.07 (d, 2H), 7.65 (s, 1H), 7.57 (t, 1H), 7.47 (m, 2H), 6.41 (d, 1H), 5.83 (t, 1H), 5.74 (bs, 1H), 4.85 (bs, 2H), 4.56 (s, 2H), 4.47 (m, 2H), 2.98 (bs, 1H), 0.88 (m, 2H), 0.65 (m, 2H).

Example 5

Preparation of Benzoic acid 4(R,S)-(2-amino-6-cyclopropylamino-purin-9-yl)-[1,3]dioxolan-2(R)-ylmethyl ester (Compound 6A and 6B)

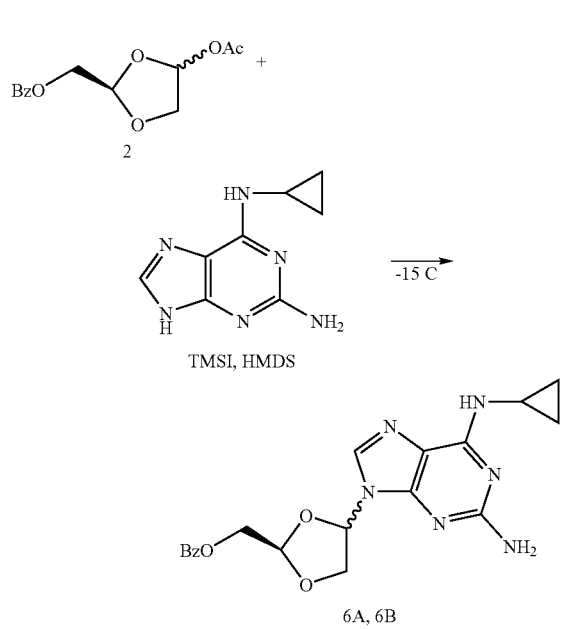

To a solution of of benzoic acid 4-acetoxy-[1,3]dioxolan-2(R)-ylmethyl ester (6.02 g, 18.8 mm) in dichloroethane (56 mL) was charged TMSI (3.2 mL) at −15° C. After the addition the reaction was stirred for 2 hours at −15° C. HMDS (5.9 mL, 28.2 mm) was added followed by 2-amino-6-cyclopropylaminopurine (3.57 g, 18.8 mm). The reaction was allowed to warm up to room temperature and was stirred for 48 hours followed by 3 hours of reflux. The reaction was cooled to room temperature and poured into saturated sodium bicarbonate solution. The mixture was filtered through a pad of Celite and the organic layer was separated. The aqueous layer was back-extracted with dichloromethane (2×20 mL). The combined organic phases were dried over sodium sulfate and concentrated to a residue. The crude product was purified by flash chromatography (40/60:EtOAc/Hexane followed by DCM/MeOH:25/1) to produce benzoic acid 4(R,S)-(2-amino-6-cyclopropylamino-purin-9-yl)-[1,3]dioxolan-2(R)-ylmethyl ester benzoate-cyclopropylaminopurine (2.25 g, 27% yield, cis/trans:1/1.25).

(Cis) Benzoic acid 4(R)-(2-amino-6-cyclopropylamino-purin-9-yl)-[1,3]dioxolan-2(R)-ylmethyl ester, δ (CDCl₃); 8.03 (d, 2H), 7.74 (s, 1H), 7.58 (t, 1H), 7.43 (m, 2H), 6.38 (d, 1H), 5.80 (bs, 1H), 5.43 (t, 1H), 4.90 (bs, 2H), 4.62 (s, 2H), 4.57 (m, 1H), 4.30 (d of d, 1H), 3.05 (bs, 1H), 0.88 (m, 2H),

Example 6

Preparation of [4(R)-(2-Amino-6-chloro-purin-9-yl)-[1,3]dioxolan-2(R)-yl]-methanol (Compound 4)

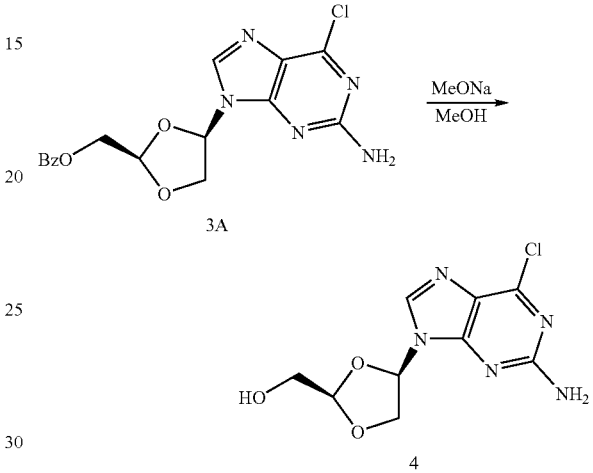

Benzoic acid 4(R)-(2-amino-6-chloro-purin-9-yl)-[1,3]dioxolan-2(R)-ylmethyl ester (2.4 kg, 6.3 moles) and methanol (6.24 L) were combined under inert atmosphere. 25% MeONa/MeOH (33.6 g) was added at room temperature and the reaction mixture was stirred for 16-24 hours. The reaction was monitored by HPLC for complete deprotection of the benzoate ester. The reaction mixture was cooled to 2° C. for 2 hours. The solids were collected by filtration and dried in vacuo to give the desired compound (1.2 kg, 71% yield).

δ (DMSO); 8.25 (s, 1H), 7.00 (s, 2H), 6.25 (d, 1H), 5.13 (t, 1H), 5.04 (s, 1H), 4.54 (d, 1H), 4.18 (d of d, 1H), 3.58(m, 2H).

Example 7

Preparation benzoic acid 4(R)-(2-amino-6-cyclopropylamino-purin-9-yl)-[1,3]dioxolan-2(R)-ylmethyl ester (Compound 6A)

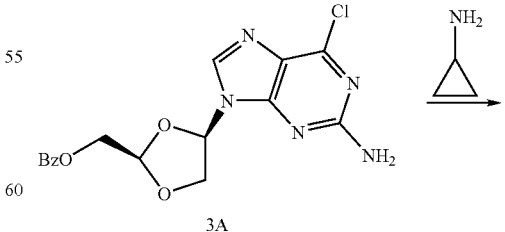

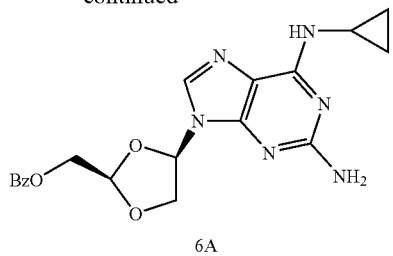

6A

Benzoic acid 4(R)-(2-amino-6-chloro-purin-9-yl)-[1,3]dioxolan-2(R)-ylmethyl ester (1266 g, cis/trans:1.9/1), ethanol (20 L), and cyclopropylamine (643 g) were refluxed for 16 hours. The reaction mixture was cooled and concentrated to a residue. The residue was dissolved in dichloromethane (3.6 L) and agitated with an aqueous solution of sodium bicarbonate for 30 minutes. After settling the organic layer was separated and the aqueous was back-extracted with dichloromethane (2×750 mL). The combined organic layers were concentrated to give a yellow-brown foam (1304 g) of material (9) which is suitable for reaction in the subsequent deprotection step in NH$_3$/MeOH.

Example 8

Preparation of [4(R)-(2-Amino-6-cyclopropylamino-purin-9-yl)-[1,3]dioxolan-2(R)-yl]-methanol (Compound 5)

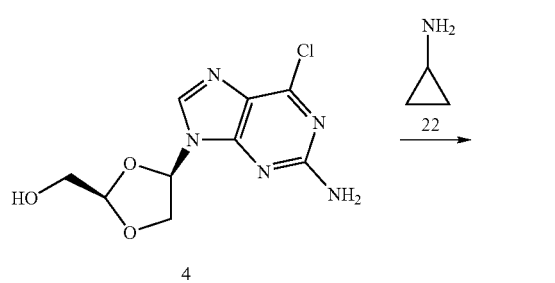

[4(R)-(2-Amino-6-chloro-purin-9-yl)-[1,3]dioxolan-2(R)-yl]-methanol (1.2 kg, 4.5 moles), ethanol (15.2 L) and cyclopropylamine (756 g) were refluxed under nitrogen for 16 hours. The reaction was monitored for completion by HPLC. Once completed the reaction mixture was hot-filtered and allowed to cool to 0° C. slowly. The solids were filtered and subsequently recrystallized from ethanol to give [4(R)-(2-Amino-6-cyclopropylamino-purin-9-yl)-[1,3]dioxolan-2 (R)-yl]-methanol (1.0 kg, 77%).

δ (DMSO); 7.84 (s, 1H), 7.37 (bs, 1H), 6.20 (d, 1H), 5.91 (bs, 2H), 5.15 (t, 1H), 5.02 (t, 1H), 4.42 (d, 1H), 4.18 (m, 1H), 3.58 (m, 2H), 3.02 (bs, 1H), 0.64 (m, 2H), 0.57 (m, 2H)

Example 9

Preparation [4(R)-(2-Amino-6-cyclopropylamino-purin-9-yl)-[1,3]dioxolan-2(R)-yl]-methanol (Compound 5)

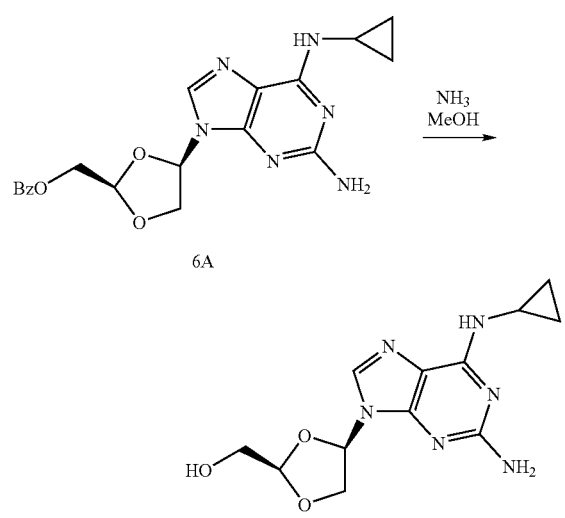

Benzoic acid 4(R)-(2-amino-6-cyclopropylamino-purin-9-yl)-[1,3]dioxolan-2(R)-ylmethyl ester crude (1304 g) was stirred with NH$_3$/MeOH (20 L, 2M) for 20 hours at room temperature. Excess ammonia was removed by sparging nitrogen gas through the reaction mixture. The volatiles were removed in vacuo to give a black syrup which was further purified by column chromatography (MeOH/DCM:25/1) to give crude final product (910 g). The crude product was crystallized from ethyl acetate/ethanol to give [4(R)-(2-Amino-6-cyclopropylamino-purin-9-yl)-[1,3]dioxolan-2 (R)-yl]-methanol (455 g, 41% yield from acetoxy-sugar).

Example 10

Preparation of Benzoic acid 4(R,S)-acetoxy-[1,3]dioxolan-2(S)-ylmethyl ester (8)

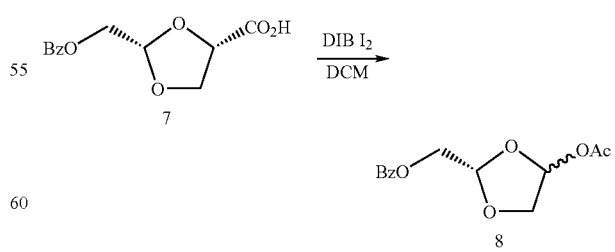

Intermediate 7 can be prepared according to known procedures described in U.S. Pat. No. 6,022,876 by CHUNG, K. Chu et al Feb. 8, 2000 and U.S. Pat. No. 5,817,667 by CHUNG, K. Chu et al Oct. 6, 1998.

To a solution of DIB (882.3 g, 2.74 moles, 1.3 eq) and iodine (159.9 g, 0.63 mole, 0.3 eq) in dichloromethane (3.5 L) at room temperature (20-25° C.) was added a solution of acid (532.0 g, 2.10 mole, 1.0 eq) in dichloromethane (3.2 L) over 2 hours (during the addition the batch temperature reached 40° C.). The solution was then stirred for an additional 2 hours at room temperature in the presence of visible light. TLC showed the absence of starting material. The reaction was quenched slowly (keep batch temperature <25° C.) with a solution of sodium thiosulfate pentahydrate (568 g, 2.29 mole, 1.09 eq) in water (4.0 L) and was stirred for 15 minutes. The layers were allowed to separate and the bottom organic phase was collected. The aqueous phase was back-extracted with dichloromethane (2×630 mL) and the organic phases were combined and dried over sodium sulfate. The sodium sulfate was filtered and the solvent was evaporated to give a brown oil (955 g) which was sparged (25-50 torr, bath temperature 80° C., batch temperature 40-65° C., 10 hours) with nitrogen to yield crude product (500 g) which was suitable for use in the subsequent sugar-base coupling. HPLC qualitative analysis showed that the crude contained (295 g, 59.1% area) of diastereomeric acetoxy-sugar, (135 g, 27.2% area) of diastereomeric homo-coupled acyloxy-sugar and (11.3 g, 2.3% area) iodobenzene. The yield of usable material was estimated as follows: Purity=HPLC % of acetoxy sugar+ ½(HPLC % of homo-coupled acyloxy-sugar)=59.1%+ ½(27.2%)=72.7% Corrected yield of usable material=72.7%×500 g=363.5 g (1.37 moles, 65% yield). (cis) Benzoic acid 4(R)-acetoxy-[1,3]dioxolan-2(R)-ylmethyl ester. δ (CDCl$_3$); 8.08 (d, 2H), 7.58 (m, 1H), 7.47 (m, 2H), 6.40 (d, 1H), 5.48 (t, 1H), 4.49 (m, 2H), 4.20 (d, 1H), 4.06 (d of d, 1H), 2.02 (s, 3H): (trans) Benzoic acid 4(R)-acetoxy-[1,3]dioxolan-2(S)-ylmethyl ester δ (CDCl$_3$); 8.05 (d, 2H), 7.55 (m, 1H), 7.45 (m, 2H), 6.47 (d, 1H), 5.57 (t, 1H), 4.47 (d, 2H), 4.24 (d of d, 1H), 4.00 (d of d, 1H), 2.11 (s, 3H).

Example 11

Preparation of Benzoic acid 4(R,S)-acetoxy-[1,3]dioxolan-2(S)-ylmethyl ester (8)

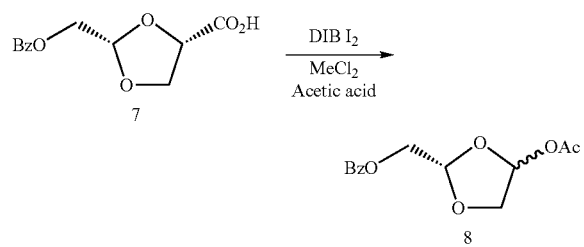

A solution of cis-acid (2.39 kg) in dichloromethane (4.2 kg) was added in 5 portions (each portion was added over 2 hours keeping the batch temperature less than 30° C.) to a solution of DIB (4.03 kg), iodine (1.06 kg) and acetic acid (1.50 kg) in dichloromethane (12.6 kg) in the presence of a 100 watt tungsten lamp. The reaction mixture was stirred until TLC showed the absence of starting material. The reaction was cooled to 15° C. and a solution of sodium thiosulfate (1.89 kg) in water (10.5 kg) was slowly added keeping the batch temperature below 25° C. The contents were stirred for 30 minutes. The layers were allowed to separate for 30 minutes and the bottom organic phase was collected. Water (10.5 kg) was charged to the organic phase. The contents were stirred for 30 minutes. The layers were allowed to separate for 30 minutes and the bottom organic phase was collected. A solution of sodium carbonate (0.2 kg) in water (10.5 kg) was charged to the organic phase. The contents were stirred for 30 minutes. The layers were allowed to separate for 30 minutes and the bottom organic phase was collected. The organic phase was reduced in volume in vacuo until the distillation stops (maximum bath temperature 45° C.). The crude product was column chromatographed to give a cis-trans mixture of acetoxy sugar (15) (2.1 kg, 96.6% pure, 93.9% yield).

Example 12

Preparation of Benzoic acid 4(R,S)-(4-acetylamino-2-oxo-2H-pyrimidin-1-yl)-[1,3]dioxolan-2(S)-ylmethyl (9A and 9B)

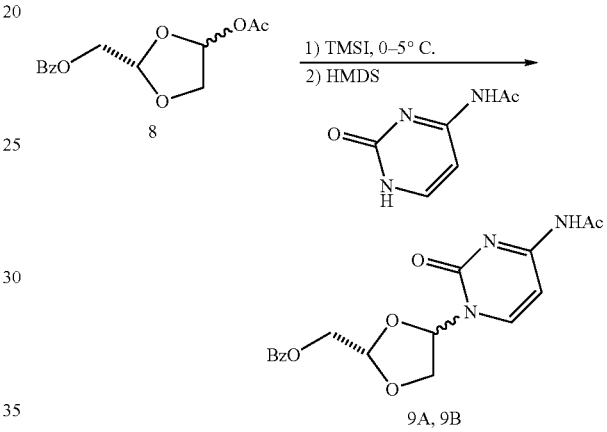

A solution of Benzoic acid 4(R,S)-acetoxy-[1,3]dioxolan-2(S)-ylmethyl ester (20 g) in methylene chloride (400 mL) was cooled to 0-5° C. and TMSI (19.54 g, 1.3 eq) was added with stirring at 0-5° C. until the formation (ca. 2 hours) of the iodosugar was completed by TLC. To the iodosugar solution was added HMDS (36.36 g, 3.0 eq), followed by N-acetylcytosine (10.35 g, 0.9 eq). The reaction mixture was stirred at 0-5° C. and was monitored by TLC. After the reaction (3 hours) was completed 10% sodium thiosulfate solution was charged to the reaction mixture and the resulting mixture was stirred for 15 minutes. The organic layer was separated and was treated with 5% sodium bicarbonate solution (100 mL) and was filtered. The organic layer was separated and was concentrated under vacuum at 50° C. (bath temperature) until distillation stops. The solid residue (28.21 g, 120% yield) was treated with acetone (129 mL) and isopropyl acetate (294 mL). The mixture was heated at reflux for 15-30 minutes and was cooled to ambient temperature over 1 hour. The solid precipitate was filtered and was dried to afford a cis/trans mixture of protected cytosine-dioxolane (16.9 g, 72% yield, 4/1:cis/trans). The 2 isomers were separated by crystalization. (Cis) Benzoic acid 4(S)-(4-acetylamino-2-oxo-2H-pyrimidin-1-yl)-[1,3]dioxolan-2(S)-ylmethyl: d(CDCl$_3$); 9.13 (s, 1H) 8.15 (d, 1H), 8.05 (d, 2H), 7.65 (t, 1H), 7.50 (t, 2H) 7.25 (d, 1H), 6.26 (m, 1H), 5.37 (t, 1H), 4.82 (d of d, 1H), 4.61 (d of d, 1H), 4.31 (m, 2H), 2.24 (s, 3H): (Trans) Benzoic acid 4(R)-(4-acetylamino-2-oxo-2H-pyrimidin-1-yl)-[1,3]dioxolan-2(S)-ylmethyl (CDCl$_3$); 8.70 (bs, 1H), 8.06 (d, 2H), 7.85 (d, 1H), 7.61 (t, 1H), 7.48 (m, 3H), 6.22 (m, 1H), 5.78 (t, 1H), 4.64 (q, 1H), 4.50 (m, 2H), 4.15 (d of d, 1H), 2.24 (s, 3H)

Example 13

Preparation of 4-Amino-1-{2(S)-hydroxymethyl-[1,3]dioxolan-4(S)-yl}-1H-pyrimidin-2-one (10)

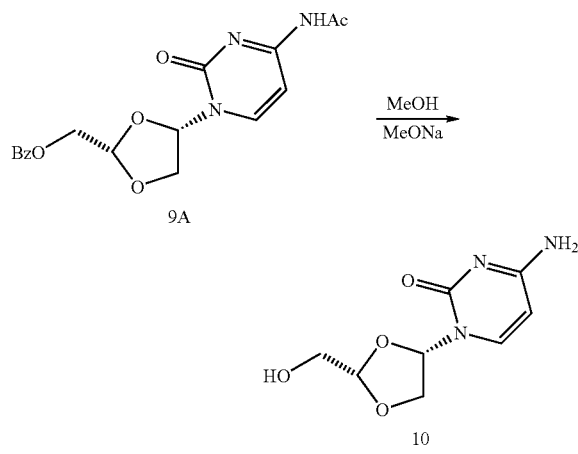

Protected cis cytosine-dioxolane (139.0 g, 0.387 moles, 1.0 eq) was slurried in MeOH/EtOH:1/1 (560 mL, 4 vol) at room temperature (20° C.). Solid MeONa (1.4 g, 95%, 1.33 g (corrected), 24.6 mm, 6.36 m %) was charged to the reaction mixture. The reaction was monitored by TLC (MeCl$_2$/MeOH:9/1) for the disappearance of starting material (Rf 0.47) and the appearance of product (Rf 0.06). The reaction mixture appearance changes from a slurry to a solution as the reaction progresses. After 3 hours of stirring at room temperature the reaction was completed. The reaction mixture was concentrated in vacuo to ½ the original volume (to 300 mL). Toluene (400 mL) was charged to the reaction mixture. The reaction mixture was further concentrated in vacuo to a final volume of 500 mL. The resulting slurry was cooled in an ice bath for 1 hour. The solids were filtered and were washed with ethyl acetate (2×75 mL). The solids were dried at room temperature under high vacuum until constant weight to yield cytosine-dioxolane (82.2 g, >99% yield, purity 99.64%). (DMSO); 7.79 (d, 1H), 7.20 (bs, 1H), 7.12 (bs, 1H), 6.17 (t, 1H), 5.70 (d, 1H), 5.16 (t, 1H), 4.90 (t, 1H), 4.05 (m, 2H), 3.63 (m, 2H).

We claim:

1. A process for producing a dioxolane compound of formula III

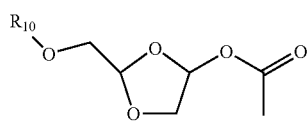

said process comprising:
reacting a dioxolane compound of formula IV in a solvent;

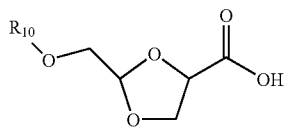

in the presence of diacetoxy iodobenzene and I$_2$, wherein said process is conducted using a source of energy; and wherein R$_{10}$ is a hydroxyl protecting group.

2. The process according to claim 1, wherein the dioxolane compound of formula IV is added to a mixture of diacetoxy iodobenzene and I$_2$.

3. The process according to claim 1, further comprising reacting said dioxolane compound of formula IV in the presence acetic acid, wherein the dioxolane compound of formula IV is added to a mixture of diacetoxy iodobenzene, I$_2$ and acetic acid.

4. The process according to claim 1, wherein R$_{10}$ is C$_{1-6}$ alkyl, C$_{6-12}$ aryl, C$_{6-12}$ arylalkyl, CO—C$_{1-6}$ alkyl, CO—C$_{1-6}$ alkoxy, CO—C$_{6-12}$ aryloxy, or CO—C$_{6-12}$arylalkyl.

5. The process according to claim 4, wherein R$_{10}$ is acetyl, pivaloyl, benzoyl, isopropyloxycarbonyl, or benzyl.

6. The process according to claim 4, wherein R$_{10}$ is benzoyl.

7. The process according to claim 1, wherein the solvent is toluene or dichloromethane.

8. The process according to claim 7, wherein the solvent is dichloromethane.

9. The process according to claim 1, wherein diacetoxy iodobenzene is used in a molar ratio of about 1.0 equivalent to about 2.5 equivalents with respect to the dioxolane compound of formula III.

10. The process according to claim 9, wherein diacetoxy iodobenzene is used in a molar ratio of about 1.1 equivalent to about 1.5 equivalents with respect to the dioxolane compound of formula III.

11. The process according to claim 1, wherein I$_2$ is used in a molar ratio of about 0.1 equivalent to about 1.0 equivalent with respect to the dioxolane compound of formula III.

12. The process according to claim 11, wherein I$_2$ is used in a molar ratio of about 0.3 equivalent to about 0.5 equivalent with respect to the dioxolane compound of formula III.

13. The process according to claim 1, wherein the source of energy is light.

14. The process according to claim 13, wherein the source of energy is tungsten lamp light.

15. The process according to claim 13, wherein the source of energy is daylight.

16. The process according to claim 1, wherein the source of energy is heat.

17. A process for producing a dioxolane compound of formula III:

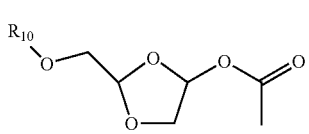

said process comprising:
reacting a dioxolane compound of formula IV in a solvent in the presence of diacetoxy iodobenzene and $I_2$;

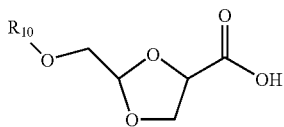

wherein $R_{10}$ is acetyl, pivaloyl, benzoyl, benzyl, or isopropyloxycarbonyl, and
said dioxolane compound of formula IV is added to a mixture of diacetoxy iodobenzene and $I_2$, and said process is conducted using a source of energy.

18. A process according to claim 17, wherein diacetoxy iodobenzene is used in a molar ratio of about 1.0 equivalent to about 2.5 equivalents with respect to the dioxolane compound of formula III.

19. A process according to claim 17, wherein diacetoxy iodobenzene is used in a molar ratio of about 1.1 equivalent to about 1.5 equivalents with respect to the dioxolane compound of formula III.

20. A process according to claim 17, wherein $I_2$ is used in a molar ratio of about 0.1 equivalent to about 1.0 equivalent with respect to the dioxolane compound of formula III.

21. A process according to claim 17, wherein $I_2$ is used in a molar ratio of about 0.3 equivalent to about 0.5 equivalent with respect to the dioxolane compound of formula III.

22. A process for producing a dioxolane compound of formula III:

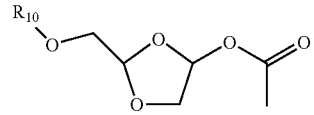

said process comprising:
reacting a dioxolane compound of formula IV in a solvent in the presence of diacetoxy iodobenzene and $I_2$;

IV wherein
the dioxolane compound of formula IV is added to a mixture of diacetoxy iodobenzene, $I_2$ and acetic acid,
$R_{10}$ is acetyl, pivaloyl, benzoyl, benzyl, or isopropyloxycarbonyl; and
said process is conducted using a source of energy.

23. A process according to claim 22, wherein diacetoxy iodobenzene is used in a molar ratio of about 1.0 equivalent to about 2.5 equivalents with respect to the dioxolane compound of formula III.

24. A process according to claim 22, wherein diacetoxy iodobenzene is used in a molar ratio of about 1.1 equivalent to about 1.5 equivalents with respect to the dioxolane compound of formula III.

25. A process according to claim 22, wherein $I_2$ is used in a molar ratio of about 0.1 equivalent to about 1.0 equivalent with respect to the dioxolane compound of formula III.

26. A process according to claim 22, wherein $I_2$ is used in a molar ratio of about 0.3 equivalent to about 0.5 equivalent with respect to the dioxolane compound of formula III.

* * * * *

UNITED STATES PATENT AND TRADEMARK OFFICE
CERTIFICATE OF CORRECTION

PATENT NO. : 7,442,813 B2  Page 1 of 1
APPLICATION NO. : 11/713724
DATED : October 28, 2008
INVENTOR(S) : Gregory Bydlinski It is certified that error appears in the above-identified patent and that said Letters Patent is hereby corrected as shown below:

Column 20, lines 18-19, reads "the presence acetic" should read -- the presence of acetic --

Signed and Sealed this

Tenth Day of November, 2009

David J. Kappos
*Director of the United States Patent and Trademark Office*